(12) United States Patent
Hoon et al.

(10) Patent No.: US 8,084,246 B2
(45) Date of Patent: Dec. 27, 2011

(54) METHOD AND APPARATUS FOR IN VIVO SURVEILLANCE OF CIRCULATING BIOLOGICAL COMPONENTS

(75) Inventors: David Hoon, Los Angeles, CA (US); Bret Taback, Santa Monica, CA (US); Samuel Shaolian, Newport Beach, CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

(21) Appl. No.: 12/109,252

(22) Filed: Apr. 24, 2008

(65) Prior Publication Data

US 2008/0241847 A1 Oct. 2, 2008

Related U.S. Application Data

(63) Continuation of application No. 10/927,960, filed on Aug. 27, 2004, now abandoned.

(60) Provisional application No. 60/531,928, filed on Dec. 22, 2003.

(51) Int. Cl.
C12M 1/34 (2006.01)

(52) U.S. Cl. .................................. 435/287.1

(58) Field of Classification Search ........................ None
See application file for complete search history.

(56) References Cited

U.S. PATENT DOCUMENTS

| | | | |
|---|---|---|---|
| 4,650,547 A | 3/1987 | Gough | |
| 5,001,051 A | 3/1991 | Miller et al. | |
| 5,424,187 A | 6/1995 | Shor et al. | |
| 5,804,453 A | 9/1998 | Chen | |
| 5,859,937 A * | 1/1999 | Nomura | 385/12 |
| 5,938,595 A | 8/1999 | Glass et al. | |
| 5,981,297 A | 11/1999 | Baselt | |
| 6,214,560 B1 | 4/2001 | Yguerabide et al. | |
| 6,235,473 B1 | 5/2001 | Friedman et al. | |
| 6,251,142 B1 | 6/2001 | Bernacca et al. | |
| 6,256,522 B1 | 7/2001 | Schultz | |
| 6,379,622 B1 | 4/2002 | Polak et al. | |
| 6,405,066 B1 | 6/2002 | Essenpreis et al. | |
| 6,449,507 B1 | 9/2002 | Hill et al. | |
| 6,465,177 B1 | 10/2002 | Hoon | |
| 6,468,657 B1 | 10/2002 | Hou et al. | |
| 6,488,704 B1 | 12/2002 | Connelly et al. | |
| 6,630,355 B1 | 10/2003 | Pivarnik et al. | |
| 6,630,356 B1 | 10/2003 | Armstrong et al. | |
| 6,649,143 B1 | 11/2003 | Contag et al. | |
| 6,656,702 B1 | 12/2003 | Yugawa et al. | |
| 6,664,111 B2 | 12/2003 | Bentsen et al. | |
| 6,673,596 B1 * | 1/2004 | Sayler et al. | 435/288.7 |
| 6,673,914 B1 | 1/2004 | Hoon | |
| 6,689,603 B2 * | 2/2004 | Pompidou et al. | 435/287.2 |
| 6,706,232 B2 | 3/2004 | Hasegawa et al. | |
| 6,743,639 B1 | 6/2004 | Tondra et al. | |
| 6,746,582 B2 | 6/2004 | Heller et al. | |
| 2002/0055111 A1 * | 5/2002 | Chen et al. | 435/6 |
| 2002/0115931 A1 | 8/2002 | Strauss et al. | |
| 2003/0134100 A1 * | 7/2003 | Mao et al. | 428/304.4 |
| 2003/0175818 A1 | 9/2003 | Ross et al. | |
| 2003/0175850 A1 | 9/2003 | Ross et al. | |
| 2004/0009584 A1 * | 1/2004 | Mitra et al. | 435/287.2 |
| 2004/0092825 A1 | 5/2004 | Madar et al. | |
| 2004/0100284 A1 | 5/2004 | Lee et al. | |
| 2004/0191246 A1 * | 9/2004 | Connelly et al. | 424/140.1 |
| 2005/0153379 A1 | 7/2005 | Hoon et al. | |
| 2006/0183223 A1 * | 8/2006 | King et al. | 435/372 |
| 2009/0011445 A1 | 1/2009 | Hoon et al. | |

FOREIGN PATENT DOCUMENTS

WO   WO 99/34191   7/1999

OTHER PUBLICATIONS

Notice of Allowance, U.S. Appl. No. 10/927,959, Apr. 3, 2008 (Ref. No. 1 above).
EP 04 81 5451, Supplementary Partial European Search Report dated Apr. 18, 2008.
PCT Application No. PCT/US04/43376, filed Dec. 22, 2004, entitled *Method and Apparatus for in Vivo Collection and Surveillance of Circulating Biological Components*, PCT International Search Report and Written Opinion of the International Searching Authority.
Greenberg, et al., "Detection of hepatocyte growth factor/scatter factor receptor (c-Met) in axillary drainage after operations for breast cancer using reverse transcriptase—polymerase chain reaction," Breast Cancer Research, vol. 5, No. 3, pp. R71-R76.
Savran, et al., "Micromechanical Detection of Proteins Using Aptamer-Based Receptor Molecules," Analytical Chemistry, p. Est: 4.4, pp. A-E.
Fritz, et al "Electronic detection of DNA by its intrinsic molecular charge," PNAS, vol. 99, No. 22, Oct. 29, 2002, pp. 14142-14146.
Selected Abstracts, *New Applications of Cellular and Molecular Technology in Breast Cancer Management*, An Unofficial Satellite Event at San Antonio Breast Cancer Symposium, 2003, 14 pages.
Russo, "*Integrated Silicon Field-Effect Sensors and Microfluidics for Biomolecular Detection*," Submitted to the Department of Electrical Engineering and Computer Science, Massachusetts Institute of Technology, Feb. 9, 2004, 60 pages.
Vo-Dinh, et al., "*Fiberoptic Immunosensors*," Fiber Opt. Chem. Sensors and Biosensors, O.S. Wolfbeis, Ed., vol. 2, Chapter 17, pp. 217-223, CRC Press, Boca Raton, FL, (1991).
Office Action for U.S. Appl. No. 12/209,091 mailed Jun. 23, 2010 in 17 pages.

* cited by examiner

*Primary Examiner* — Ann Lam
(74) *Attorney, Agent, or Firm* — Knobbe, Martens, Olson & Bear LLP

(57) ABSTRACT

The invention relates generally to in vivo collection of circulating molecules, tumor cells and other biological markers using a collecting probe. The probe is configured for placement within a living organism for an extended period of time to provide sufficient yield of biological marker for analysis.

23 Claims, 9 Drawing Sheets

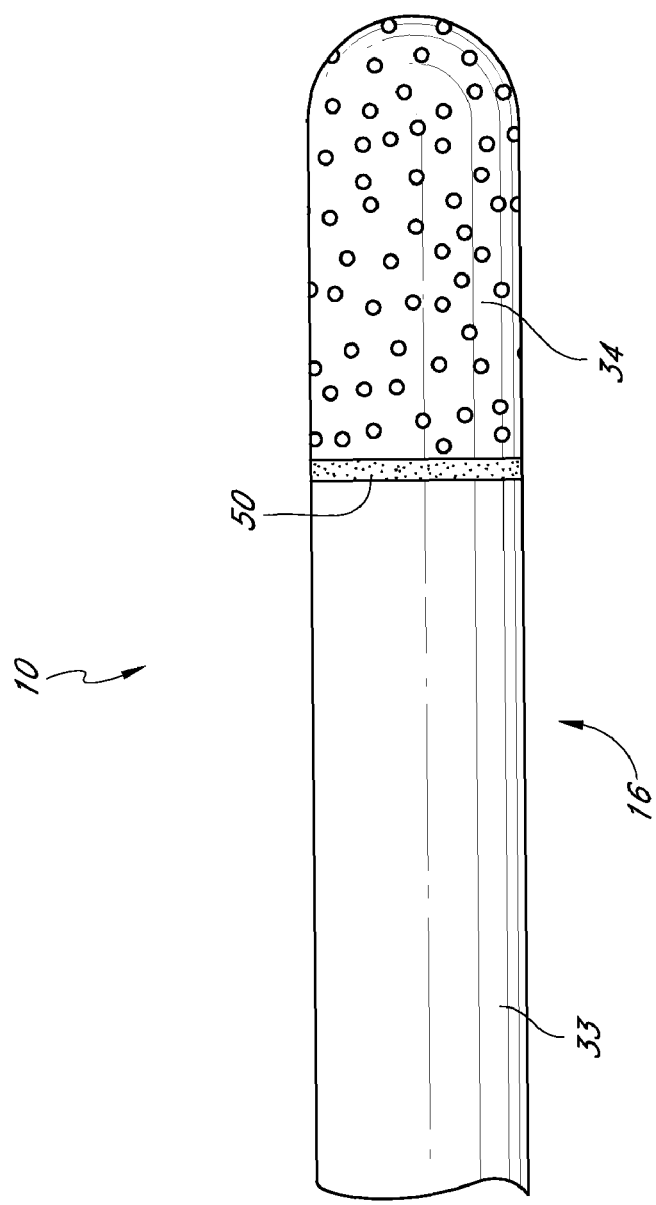

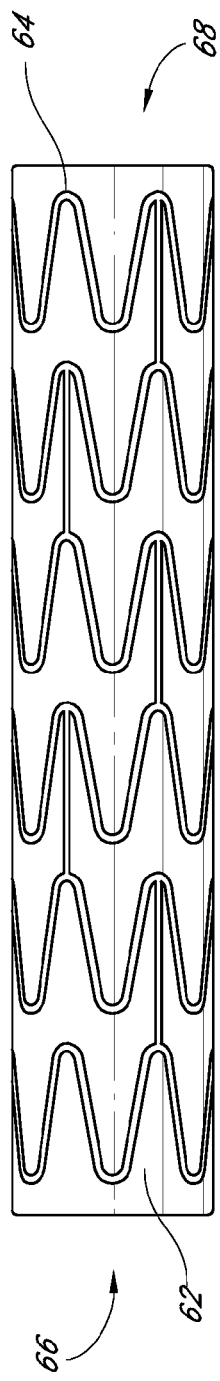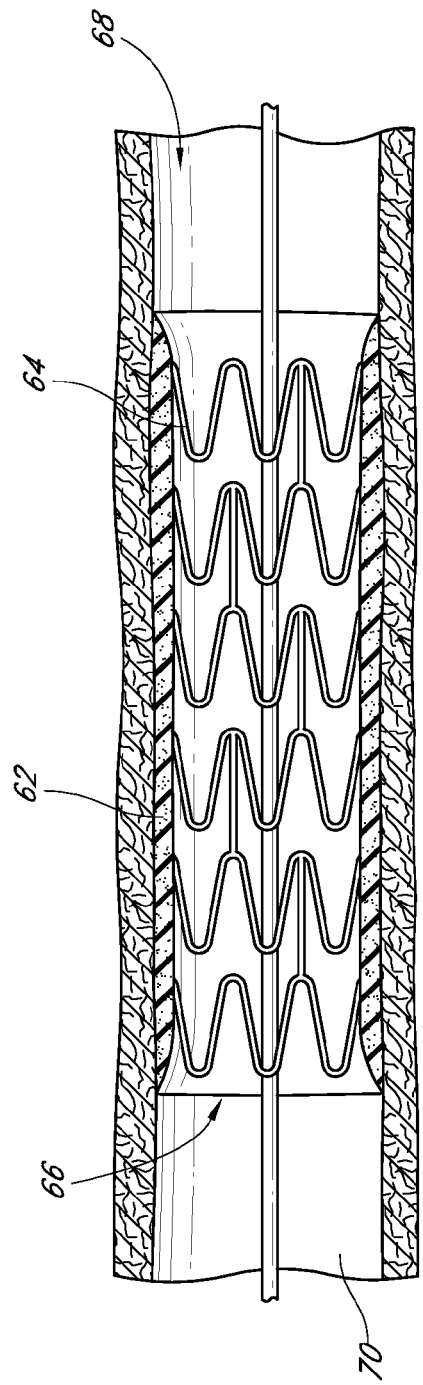

METHOD AND APPARATUS FOR IN VIVO SURVEILLANCE OF CIRCULATING BIOLOGICAL COMPONENTS

CROSS-REFERENCE TO RELATED APPLICATIONS

The present application is a continuation of U.S. patent application Ser. No. 10/927,960 filed on Aug. 27, 2004, which claims priority under 35 U.S.C. §119(e) to U.S. Provisional Application No. 60/531,928 filed on Dec. 22, 2003, the disclosure of which is incorporated by reference herein in its entirety.

BACKGROUND OF THE INVENTION

1. Field of the Invention

This invention relates generally to devices and methods for collecting and/or detecting biological components in vivo over a period of time. The detection and/or analysis of the biological components collected by the devices may be performed in vivo or ex vivo.

2. Description of the Related Art

Cancer is one of the leading causes of disease, being responsible for 563,700 deaths in the United States each year (Jemal A et al., Cancer statistics, 2004, CA Cancer J Clin. 2004 January-February; 54(1):8-29). For example, breast cancer is the most common form of malignant disease among women in Western countries and, in the United States, is the most common cause of death among women between 40 and 55 years of age (Forrest A P, Screening and breast cancer incidence, J Natl Cancer Inst. 1990 Oct. 3; 82(19):1525-6.). The incidence of breast cancer is increasing, especially in older women, but the cause of this increase is unknown. Malignant melanoma is another form of cancer whose incidence is increasing at a frightening rate, at least sixfold in the United States since 1945, and is the single most deadly of all skin diseases (Jemal et al., 2004).

One of the most devastating aspects of cancer is the propensity of cells from malignant neoplasms to disseminate from their primary site to distant organs and develop into metastases. The early spread of viable tumor cells is considered a hallmark in cancer progression. Despite advances in surgical treatment of primary neoplasms and aggressive therapies, most cancer patients die as a result of metastatic disease. Animal tests indicate that a substantial frequency of circulating cancer cells from solid tumors establish successful metastatic colonies (Fidler, 1993). Studies have found that the detection of circulating metastatic tumor cells and circulating tumor DNA in the blood of cancer patients correlates with cancer progression. (Hoon D S, et al., Molecular markers in blood as surrogate prognostic indicators of melanoma recurrence, Cancer Res. 2000 Apr. 15; 60(8):2253-7, and Taback B, et al., Circulating DNA microsatellites: molecular determinants of response to biochemotherapy in patients with metastatic melanoma, J. Natl. Cancer Inst. 2004 Jan. 21; 96(2): 152-6, herein incorporated in their entirety by reference)

Thus, the detection of occult cancer cells, DNA and tumor markers in the circulation is important in assessing the level of tumor progression and metastasis. Because subclinical metastasis can remain dormant for many years, traditional surveillance measures such as radiological monitoring with CT scans or MRI and nodal biopsy may lack the sensitivity to detect early disease.

Notwithstanding the foregoing, there remains a need for improved methods and devices for detecting biological components of disease.

SUMMARY OF THE INVENTION

In one embodiment of the invention, a biological surveillance probe for detecting disease is provided. The probe comprises an elongate body having a proximal end and a distal end, a binding surface attached to the elongate body, wherein the binding surface has a microconfiguration for an increased surface area, and at least one binding partner attached to the binding surface to bind at least one complementary target. In some embodiments, the binding surface is a microporous surface or has at least one laser-drilled hole. In some embodiments, the binding surface been configured by vapor deposition, physical vapor deposition, chemical vapor deposition, sputtering, reactive sputtering, sintering or vacuum deposition. The binding surface may comprise a material selected from a group comprising a microporous polymer, nanotube, metal, non-metal, ceramic or combination thereof. The elongate body may be a catheter body or a stent support. The binding surface may be a polymeric jacket. In some embodiments, the probe may further comprise at least one optically sensitive dye engaged to the binding surface, a fibrin-deposition resistant component, at least one anti-thrombotic agent or antimicrobial agent engaged to the binding surface. An atraumatic tip may be attached to the distal end of the elongate body.

In another embodiment of the invention, a method for collecting biological markers is provided. The method comprises the steps of providing a collecting probe comprising a microconfigured binding surface and at least one binding agent affixed to the binding surface for binding a marker, positioning at least a portion of the probe in an anatomical structure of a living organism; maintaining the probe in a general position for a specified period of time; and removing the probe from the living organism. The method may further comprise the steps of binding at least marker at a first point in time; and binding at least one marker at a second point in time. The method may also comprise binding at least one marker at a about first peak in marker concentration and binding at least one marker at about a second peak in marker concentration. The method may further comprise analyzing the probe for markers bound to the binding agent. The analyzing step may be performed ex vivo.

Several embodiments of the present invention provides these advantages, along with others that will be further understood and appreciated by reference to the written disclosure, figures, and claims included herein.

BRIEF DESCRIPTION OF THE DRAWINGS

The structure and operation of the invention will be better understood with the following detailed description of embodiments of the invention, along with the accompanying illustrations, in which:

FIGS. 5A and 5B are schematic side and front elevational views of one embodiment of the probe comprising a proximal section joined to a distal zone;

FIG. 8A is a schematic of one embodiment of the probe comprising a stent with a polymer fabric collecting surface; FIG. 8B is a cross sectional schematic view of the probe from FIG. 8A within a blood vessel.

DETAILED DESCRIPTION OF THE PREFERRED EMBODIMENT

Figure 1:
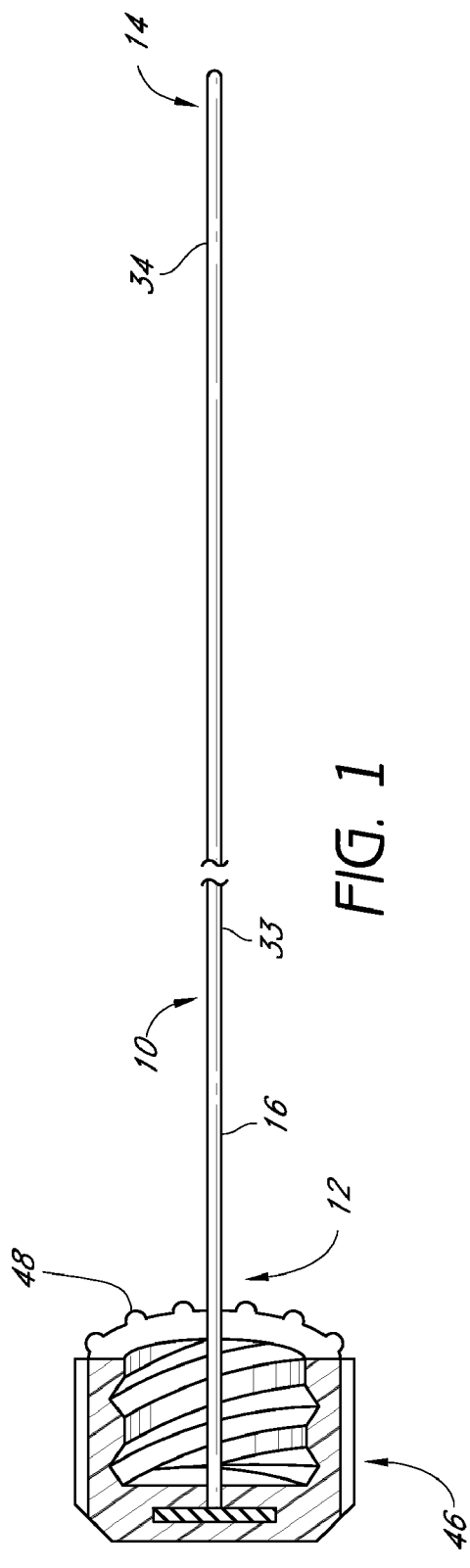
FIG. 1 is a cross sectional view depicting one embodiment of a probe capable of collecting biological components.

The detection of occult cancer cells and other biological markers has shown promise in the diagnosis and treatment of disease. For example, the monitoring of patients' blood for circulating tumor cells and other markers may prove advantageous in detecting early tumor progression before metastasis to other organs occurs. Circulating nucleic acids, tumor cells and proteins can be detected in the blood (inclusive of plasma and serum), bone marrow, cavity fluids and cerebrospinal fluid (CSF) of cancer patients which may serve as risk stratification factors, markers for the presence of clinical disease, predictors of subclinical and/or minimal residual disease presence, determinants of treatment response and disease progression, and prognosticators of patient outcome. Other body fluids shown to have the above tumor cells, protein markers, carbohydrate markers or nucleic acids include urine, pleural fluids and peritoneal fluids (ascites). However, assessment of these molecules/tumor cells or components thereof requires a blood sample, which is collected at a single time-point or at multiple time points by deliberate invasion of body tissue (i.e. needle stick).

These methods are often limited by the intermittent and/or low-level presence of cancer cells and markers in the blood. Although new amplification and detection techniques, such as immunochemistry, flow cytometry and reverse transcriptase polymerase chain reaction, aid in the detection of early disease markers, these techniques may fail to overcome sampling errors inherent in the blood draws. Because of the constant circulating nature of blood and the limited volume in a particular blood draw, evaluating a single blood sample at one time-point may not accurately represent the quantity and quality of circulating nucleic acids, tumor cells, proteins or other tumor markers for diagnosis, prognosis and monitoring of disease. Sampling error can contribute to the frequent false-negative results found with post-treatment cancer surveillance.

A major problem in detecting tumor cells and tumor markers in blood is that they are not released at any particular time point. Therefore, the probability of detecting the presence of tumor cells or markers may vary or may be unpredictable. In addition, it is known that for certain biological markers, blood flow and release of these markers from tissues are diurnally related and influenced by physical activity of an individual (i.e., climbing stairs). Circulating nucleic acids, tumor cells, proteins etc as described above (here to fore termed circulating molecules or cells or products will be referred as markers or CMC) may also be released transiently into the blood stream by other physiological events and external influences. Repetitive sampling without repetitive invasive procedures would improve the accuracy and sensitivity of detecting molecules circulating in blood.

CMCs appear to circulate in varying levels/concentrations throughout a person's disease course as well as during a single day and or in response to environmental manipulations such as treatment with chemotherapy, hormonal therapy, immunotherapy and radiotherapy, as well as with administration of medications. The variations in the stability of these CMCs found in the blood or other body fluids add to the inherent difficulties of an assay that evaluates blood at a single time point. Serial assessment of blood would increase the probability of identifying CMCs and therefore improve their utility as prognostic, predictive and diagnostic assays. However, serial assessments of patients' blood require repeated patient needle sticks which are impractical, inconvenient and uncomfortable to the patient.

A more practical and less intrusive approach would be to introduce a collecting device, probe, biomaterial adhesive matrix, chromatography affinity surface chip or probe, biochip, or particle into the body that would come in direct contact with the blood or body fluid over a period of time. This product can then be assessed, in vivo or ex vivo, after an interval of elapsed time to provide a more accurate evaluation of those CMCs. One embodiment of the invention comprises a percutaneously inserted device that resides indwelling in the bloodstream and is coated with or contains a binding partner such as nucleotides (i.e.: oligos, LNAs (locked nucleic acids), PNAs (peptide nucleic acids), cDNA, nucleic acid probes, chromatographic affinity probes or fragments thereof or their derivatives, complementary fragments or larger) antibodies (i.e.: monoclonal, polyclonal, FAb fragments, etc) proteins or any biological or synthetic material (i.e. biotin-avidin) that is complementary to the CMC in question and that can be assessed in vivo or ex vivo. The desired binding partner(s) are capable of binding the corresponding target marker of interest in a sufficient concentration and manner that permits retrieval of the probe after an indwelling sample period of time for qualitative or quantitative analysis of the marker.

The ex vivo concept is similar to a "dip stick" approach in assessing a body fluid for a particular molecule. The in vivo concept is a like an implantable physiological monitoring device. A device and approach of such nature will provide a great improvement over current methods of evaluating blood. The evaluation of the CMC can be in the form of conventional monitoring using established in vitro monitoring systems. For example, to detect circulating tumor cells or circulating nucleic acids, one can use RealTime quantitative PCR and oligonucleotide arrays. For detection of proteins, one can use enzyme-linked immunosorbent assay (ELISA), chromographic affinity assays, etc. For in vivo monitoring it can be through electric or thermal related impulses or direct imaging.

The detection time of the probe may be continuous, over multiple intervals, or event-driven. Inactivating the detection mechanism at times may conserve battery power. Reducing probe binding surface exposure to the body at times may also reduce fibrin deposition and other deleterious processes during periods of low yield. For example, increased core body temperature or increased serum potassium levels are correlated with cell lysis of certain cancers and detection during of these events may enhance the yield of interval collection and detection schemes. Other event-based detection periods may include time period to assess a patient's response to therapy through detection of components related to cellular death. This allows measurement of a patient's response, for example, to chemotherapy and/or radiation therapy, which can then be optimized to for treatment effect or to minimize side effects.

This device(s) can be inserted surgically, percutaneously or intravenously into the blood stream, peritoneal cavity or bone marrow such that continuous contact with circulating blood, and/or body fluids is ensured. The product can then be collected for analysis in a routine fashion or monitored. Several indwelling devices are currently available that coexist with the patient that in long-term contact with the blood and patients body fluids without inducing an adverse reaction. These devices also do not impair everyday patient activities of daily living. These devices include but are not limited to centrally or peripherally inserted intravenous catheters, pacemakers and their leads, automatic internal converter defibrillators, hemodialysis catheters, peritoneal catheters and prosthetic grafts.

One example of the proposed device is a coated catheter, guidewire or filament, chip, biomaterial and/or matrix that can be inserted through a centrally or peripherally place intravenous catheter or implantable catheter/material into body fluids such as peritoneal cavity, bone marrow, cerebrospinal fluid, etc. This device can then dwell in continuous or intermittent contact with the bloodstream and/or body fluids to improve yield of collecting tumor cells, components thereof, circulating nucleic acids, and proteins, or other items previously mentioned and or for prolonged or continuous in vivo or ex vivo monitoring of marker presence or activity. Monitoring time can vary in vivo from one to several days to weeks or longer. This may provide valuable information on markers of subclinical and/or minimal residual cancer presence and determinants of treatment response and disease progression. Such devices may also be used to monitor host states for other disease progression patterns, including but not limited to infectious processes and organ transplant rejection.

The invention described allows for continuous invasive monitoring of CMCs. Through a percutaneous approach, a catheter can be placed into the vasculature of a patient for continuous monitoring of circulating tumor cells and/or their component. Monitoring of CMCs may have diagnostic and prognostic value in patient care as well as serve as an improved mechanism for monitoring response to treatment. This indwelling catheter, for example, may be impregnated with complementary substrate which can include but are not limited to RNA, DNA, oligonucleotides, proteins, carbohydrates, antibodies, LNAs, PNAs, probes, or any component thereof and/or aforementioned in this application that has affinity for binding to the CMC. When the desired substrate is bound to the catheter, chip or any device mentioned in this context contained therein, the substrate can be quantitated and evaluated for information that can be conveyed to a self-embedded or external detector. In addition, this catheter or device (including nanoparticles, nanodevices, microfabricated devices, etc) and/or with an associated chip or other device containing complementary substrate to the source(s) for identification to which contains the bound substrate of interest can be removed for ex vivo analysis whereby the information obtained would provide both qualitative and quantitative data.

In addition to enhancing the sensitivity of detecting cancer and cancer recurrence, the invention allows assessment of circulating tumor cells also would provide a rapid monitoring system to determine if a specific therapy is effective.

In one embodiment of the invention, continuous surveillance/monitoring of circulating nucleic acids (including RNA, double stranded and single stranded DNA, chimeric RNA/DNA), tumor cells, fetal cells, transplant allogeneic cells, transfected cells, proteins, infectious disease nucleic acids, proteins, carbohydrates (including glucoproteins, gangliosides and phospholipids) in any complete components or fragment forms, is performed to assess the presence and/or progression of disease. These molecules will be detected in serum, plasma, whole blood, bone marrow, CSF, lymphatic fluid, pleural or peritoneal fluids, urine or other body fluids in patients with cancer, hyperplasia, pregnancy (including prenatal diagnosis), patients with infectious diseases symptomatic or asymptomatic with other medical conditions such as infectious disease, autoimmune diseases, inflammatory diseases, cardiovascular disease (including myocardial infarction, unstable angina and congestive heart failure), neurovascular diseases (e.g., ischemic events, stroke, anemia), pulmonary disease (including acute respiratory distress syndromes, fibrosis, pulmonary hypertension, emphysema, asthma, chronic obstructive pulmonary disease), renal disease (infection, hypertension nephropathies, nephritis, renal insufficiency and renal failure), trauma patients, organ failure, critical care patients, and transplant patients (including allogeneic and xenogeneic).

A. Binding Partners

The terms "binding partner" or "member of a binding pair" refer to molecules that specifically bind other molecules (e.g., a marker of interest) to form a binding complex such as antibody-antigen, lectin-carbohydrate, nucleic acid-nucleic acid, biotin-avidin, etc. In certain embodiments, the binding is predominantly mediated by noncovalent (e.g. ionic, hydrophobic, etc.) interactions.

One or more binding partners that specifically bind a target marker to be detected are affixed in the binding zone on the probe of the invention. The binding partner(s) used in this invention are selected based upon the target marker(s) that are to be identified/quantified. Thus, for example, where the target marker is a nucleic acid the binding partner is preferably a nucleic acid or a nucleic acid binding protein. Where the target marker is a protein, the binding partner is preferably a receptor, a ligand, or an antibody that specifically binds that protein. Where the target marker is a sugar or glycoprotein, the binding partner is preferably a lectin, and so forth. A device of the invention can include several different types of binding partners, for example, multiple nucleic acids of different sequence and/or nucleic acids combined with proteins in the same device. The latter would facilitate, e.g., simultaneous monitoring of gene expression at the mRNA and protein levels. Other combinations of different types of binding partners can be envisioned by those of skill in the art and are within the scope of the invention. Furthermore, the binding partner may be combined with an optically sensitive dye to facilitate assessment of bound CMCs.

Methods of synthesizing or isolating such binding partners are well known to those of skill in the art. For example, nucleic acids for use as binding partners in this invention can be produced or isolated according to any of a number of methods well known to those of skill in the art. In one embodiment, the nucleic acid can be an isolated naturally occurring nucleic acid (e.g., genomic and/or mitochondrial DNA, cDNA, mRNA, etc.). Methods of isolating naturally occurring nucleic acids are well known to those of skill in the art (see, e.g., Sambrook et al. (1989) Molecular Cloning—A Laboratory Manual (2nd Ed.), Vol. 1-3, Cold Spring Harbor Laboratory, Cold Spring Harbor, N.Y.).

1. Antibody-Based

Antibodies or antibody fragments for use as binding partners can be produced by a number of methods well known to those of skill in the art (see, e.g., Harlow & Lane (1988) Antibodies: A Laboratory Manual, Cold Spring Harbor Laboratory, and Asai (1993) Methods in Cell Biology Vol. 37. Antibodies in Cell Biology, Academic Press, Inc. N.Y.). In one embodiment, antibodies are produced by immunizing an animal (e.g., a rabbit) with an immunogen containing the epitope to be detected. A number of immunogens may be used to produce specifically reactive antibodies. Recombinant proteins are the preferred immunogens for the production of the corresponding antibodies. The antibodies may be monoclonal or polyclonal. Naturally occurring protein may also be used either in pure or impure form. Synthetic peptides are also suitable and can be made using standard peptide synthesis chemistry (see, e.g., Barany and Merrifield, Solid-Phase Peptide Synthesis; pp. 3-284 in The Peptides: Analysis, Synthesis, Biology. Vol. 2: Special Methods in Peptide Synthesis, Part A., Merrifield et al. (1963) J. Am. Chem. Soc., 85: 2149-2156, and Stewart et al. (1984) Solid Phase Peptide Synthesis, 2nd ed. Pierce Chem. Co., Rockford, Ill.) Preferably, human or humanized antibodies are used to prevent host anti-xenogen antibody production. These antibodies may include antibodies derived from hybridomas (tumor cells fused with antibody-producing mammalian cells), humanized chimerics, Epstein-Barr Virus transformed B-cells and transgenic antibodies.

Methods for producing polyclonal antibodies are also well known to those of skill in the art. In one embodiment, an immunogen is mixed with an adjuvant and an animal is immunized. The animal's immune response to the immunogen preparation is monitored by taking test bleeds and determining the titer of reactivity to the immunogen. When sufficient titers of antibody to the immunogen are obtained, blood is collected from the animal and an antiserum is prepared. If desired, the antiserum can be further fractionated to enrich for antibodies having the desired reactivity. The animal may be a monoclonal mouse, rat, rabbit, chicken or other animal known in the art.

Monoclonal antibodies can be obtained by various techniques familiar to those skilled in the art. In one embodiment, spleen cells from an animal immunized with a desired antigen are immortalized, commonly by fusion with a myeloma cell (See, Kohler and Milstein (1976) Eur. J. Immunol. 6: 511-519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yields of the monoclonal antibodies produced by such cells can be enhanced by various techniques, including injection into the peritoneal cavity of a vertebrate host. Alternatively, DNA sequences encoding a monoclonal antibody or a binding fragment thereof can be isolated by screening a DNA library from human B cells according to the general protocol outlined by Huse et al. (1989) Science, 246: 1275-1281. Such sequences can then be expressed recombinantly.

In one embodiment of the invention, the technique comprises attachment of an antibody or fragment of an antibody (referred to as Ab) to a device that can allow capture of protein, circulating tumor cells, DNA or RNA in the blood stream or body cavity. The device will be coated with Ab in high density. The Ab may be natural, recombinant (chimeric, Fab, scFv, etc.), or genetically engineered. Preferably the Ab will be human to prevent anti-foreign antibody responses (i.e. human antibody response to mouse antibodies; HAMA). The device can be removed after insertion into the blood stream to be monitored for biomarkers or cells it can capture. The insertion device can be a catheter, array chip, capture vessel, capture filter, and/or entrapment device. The device can be inserted for 1, 2, 3, 4 . . . 24 hrs or days or weeks. Monitoring of the captured biomarker or cells may be assessed in vivo or ex vivo utilizing known techniques depending on the biomarker or cell type. The biomarker or cells captured can be assessed quantitatively or qualitatively. In another approach the biomarker or cells captured will be monitored in vivo utilizing a signaling indicator based on electrical, colorimetric or activation signals.

In capturing cells the device would have specific Ab to detect cell surface markers of cancer cells. Cancer cells have distinct markers on their cell surface that distinguish them from normal cells. This has been demonstrated by immunohistochemistry (Racila E et al., Detection and characterization of carcinoma cells in the blood, Proc Natl Acad Sci USA. 1998 Apr. 14; 95(8):4589-94). These antibodies can be used to target epithelial origin cells, tumor cells originated from specific tissues, non-epithelial origin cells (i.e. melanoma). Circulating tumor cells are found in the blood stream and body fluids of cancer patients (Hoon DS, et al., "Detection of occult melanoma cells in blood with multiple-marker polymerase chain reaction assay" J Clin Onc. 1995 August; 13(8); 2109-16, and Hoon D S, et al., "Molecular markers in blood as surrogate prognostic indicators of melanoma recurrence" Cancer Res. 2000 Apr. 15; 60(8): 2253-7.). Tumor cells spread to distant organs via the blood stream, lymphatic ducts or body fluids or body cavities. The spread of tumor cells can eventually lead to tumor growth at distant sites from the original tumor, thus producing metastasis. Growth of metatastatic tumor sites can lead to death.

Detection of tumor cells can be used as an indicator of disease spread, tumor aggressiveness, potential to spread to other organs, and presence of disease in individuals who are otherwise diagnosed as disease-free by conventional means. Detection of tumor cells in vivo may be advantageous in some circumstances over ex vivo detection. The approach will allow better capture of early disease. One cannot predict disease spreading or volume through single blood draw of a small amount of blood or body fluid. One approach comprises catching tumor cells through a capturing system placed in the blood stream or body fluid for a longer period of time. This is may be advantageous when capturing occult circulating metastatic or leukemic tumor cells. The cell surface marker can be a protein, glycoprotein, glycolipid, peptide epitope, conformational biological epitope or multiple disease or tumor markers. The device may have more than one Ab attached to it to improve sensitivity and capturing ability. The Ab may be to multiple epitope sites of a single biomarker antigen. The tumor cells captured will be dislodged when the device is removed and assessed by the following ex vivo methods: immuno-histochemistry, DNA, mRNA and/or proteomics.

The isolation of the cells may involve physical removal or direct solvent removal specific to that biomarker's physical-chemical properties. For example DNA and RNA from tumor cells can be extracted directly from the tumor cells after isolation. Isolation of DNA or RNA can be by solvents used for nucleic acids. This can be accomplished directly or after the cells have been dislodged. RNA and DNA can be detected by hybridization to a specific probe, polymerase chain reaction (PCR) or related monitoring approach. The assessment of nucleic acids from the tumor cells can provide quantitative and qualitative analysis. Even if non tumor cells are captured, the specificity of the analysis can be optionally increased through a second tier analysis. Sensitivity of the analysis can be further enhanced through amplification of the nucleic acids by PCR or related methods, incorporating specific probes or detection systems ex vivo. Specificity and sensitivity ex vivo for the specific nucleic marker can be approached using current technologies. The DNA markers may include microsatellites, mutations, translocations, insertions, amplifications, SNPs or chromatin/DNA complexes. The RNA markers can include specific genes in whole or part in the form of mRNA.

Protein, glycoprotein, or glycolipid analysis can be detected by antibody, mass spectrophotometry, surface enhanced laser desorption/ionization time-of-flight mass spectrometry (SELDI-TOF MS), matrix-assisted laser desorption/ionisation-time of flight mass spectrometry (MALDI-TOF MS), affinity assay, chromatographic approach. The approach can be directly from the device or removal of the biomarker by some solvent, physical method or reagent to a vessel where it can be processed. The detection can be in the form of an affinity matrix chip for the specific biomarker type.

The Ab on the device can be a natural antibody produced by human or some animal B cells in the form of polyclonal or monoclonal antibody. The Ab can be a recombinant antibody that is released from transfected mammalian or prokaryotic cells. The Ab can be a fragment of an antibody such as scFV, FV or FAb fragment that has specific recognition of the biomarker or cell epitope. The Ab can be a genetically engineered Ab that has a specific attachment moiety or detection ability.

The Ab on the device can be polyclonal or monoclonal antibody to a specific epitope or multiple epitopes to a specific biomarker or epitope. It can consist of multiple Ab to multiple biomarkers. The latter will allow higher sensitivity and capturing ability.

Ab can be attached to the device such as a catheter by direct affinity attachment, chemical attachment, biological attachment or electric charge. The Ab can be coated in a vessel, tube or filter device, chip, filament, biopolymer matrix, biological material, capsule matrix inserted into a patient.

The Ab-coated device can be inserted into the venous, arterial or capillary beds of a patient. It can also be inserted into a body cavity such as peritoneal, pleural, skin tissue, or organ/tissue cavity created by surgical procedure.

2. Protein-Based

In one embodiment, the binding partner can be a binding protein. Suitable binding proteins include, but are not limited to, receptors (e.g., cell surface receptors), receptor ligands (e.g., cytokines, growth factors, etc.), transcription factors and other nucleic acid binding proteins, as well as members of binding pairs, such as biotin-avidin.

Binding proteins useful in the invention can be isolated from natural sources, mutagenized from isolated proteins, or synthesized de novo. Means of isolating naturally occurring proteins are well known to those of skill in the art. Such methods include, but are not limited to, conventional protein purification methods including ammonium sulfate precipitation, affinity chromatography, column chromatography, gel electrophoresis and the like (see, generally, R. Scopes, (1982) Protein Purification, Springer-Verlag, N.Y.; Deutscher (1990) Methods in Enzymology Vol. 182: Guide to Protein Purification, Academic Press, Inc. N.Y.). Where the protein binds a target reversibly, affinity columns bearing the target can be used to affinity purify the protein. Alternatively the protein can be recombinantly expressed with a HIS-Tag and purified using $Ni^{2+}$/NTA chromatography.

In another embodiment, the binding protein can be chemically synthesized using standard chemical peptide synthesis techniques. Where the desired subsequences are relatively short, the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond. This is typically accomplished using the same chemistry (e.g., Fmoc, Tboc) used to couple single amino acids in commercial peptide synthesizers.

The technique will involve detection of free circulating proteins, peptides or protein complexes via an affinity matrix or antibody or ligand (referred to as affinity substrate; AS) coated to a device that can allow capture of proteins, peptides or glycoproteins in the blood stream or body cavity. The device will be coated with AS in high density. The device can be removed after insertion into the blood stream to be monitored for biomarkers it can capture. The insertion device can be a catheter, array chip, capture vessel, capture filter, entrapment device. The device can be inserted for 1, 2, 3, 4 . . . 24 hrs or days or weeks. Monitoring of the captured biomarker or cells will be assessed ex vivo utilizing known techniques depending on the biomarker type. The biomarker captured can be assessed quantitatively or qualitatively. In another approach the biomarker captured will be monitored in vivo utilizing a signaling indicator based on electrical, colorimetric or activation signals.

Protein and glycoprotein analysis can be detected ex vivo by antibody, mass spectrophotometry, affinity assay, chromatographic approach. The approach can be directly from the device or removal of the biomarker by some solvent, physical method or reagent to a vessel where it can be processed.

The antibody used on the device can be a natural antibody produced by human or some animal B cells in the form of polyclonal or monoclonal antibody. The antibody can be a recombinant antibody that is released from transfected mammalian or prokaryotic cells. The antibody can be a fragment of an antibody such as scFV, FV or FAb fragment that has specific recognition of the biomarker or cell epitope. The antibody can be a genetically engineered antibody that has a specific attachment moiety or detection ability.

The AS can be in the form of affinity matrix material specific or non specific for specific protein properties. The former is preferable. For non-specific (not to a specific biomarker) the AS can be based on charge to attract hydrophilic or hydrophobic molecules. The antibody or ligand substrate on the device can be towards a specific epitope or multiple epitopes to a specific biomarker. It can consist of multiple AS to multiple biomarkers. The latter will allow higher sensitivity and capturing ability.

AS can be attached to the device such as a catheter by methods including but not limited to direct affinity attachment, chemical attachment, biological attachment or electric charge. The AS can be coated in a vessel, tube or filter device, chip, filament, biopolymer matrix, biological material, or capsule matrix inserted into a patient.

The AS coated device can be inserted into the venous, arterial or capillary beds of a patient. It can be inserted into a body cavity such as peritoneal, pleural, skin tissue, or organ/tissue cavity created by surgical procedure.

B. Affixation of Binding Partner to Probe

The desired binding partner(s) are affixed to the binding zone on the probe in a sufficient concentration and manner to be capable of binding the corresponding target marker of interest in a manner that permits retrieval of the probe after an indwelling sample period of time and qualitative or quantitative analysis of the marker. The linkage between the binding partner and the substrate surface on or attached to the probe is preferably chemically stable under both in vivo and assay conditions. The linkage may or may not produce significant non-specific binding of target analyte(s) to the substrate.

Many methods for immobilizing molecules to a variety of substrates are known in the art. For example, the binding partner can be covalently bound or noncovalently attached through specific or nonspecific bonding.

If covalent bonding between a compound and the surface is desired, the surface will usually be polyfunctional or be capable of being polyfunctionalized. Functional groups that may be present on the substrate surface and used for linking can include but are not limited to carboxylic acids, aldehydes, amino groups, cyano groups, ethylenic groups, hydroxyl groups, mercapto groups and the like. The manner of covalently linking a wide variety of compounds to various surfaces is well known and is amply illustrated in the literature. See, for example, Ichiro Chibata (1978) Immobilized Enzymes, Halsted Press, New York, and Cuatrecasas, (1970) J. Biol. Chem. 245: 3059, herein incorporated by reference.

In addition to covalent bonding, various methods for noncovalently bonding a binding partner can be used. Noncovalent binding is typically, but not necessarily, nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A or wheat germ agglutinin will bind a carbohydrate containing compound but not an unglycosylated protein. Various substrates for use in noncovalent attachment of assay components are reviewed in U.S. Pat. Nos. 4,447,576 and 4,254,082, herein incorporated by reference.

Where the binding partner is a nucleic acid or a polypeptide, the molecule can be chemically synthesized in situ, if desired. In situ nucleic acid or protein synthesis typically involves standard chemical synthesis methods, substituting photo-labile protecting groups for the usual protecting groups (e.g., dimethoxy trityl group (DMT) used in nucleic acid synthesis). Irradiation of the substrate surface at discrete locations results in selective coupling of the monomer (e.g., nucleotide or amino acid) to the growing nucleic acid(s) or polypeptide(s) at the irradiated site. Methods of light-directed polymer synthesis are well known to those of skill in the art (see, e.g., U.S. Pat. No. 5,143,854; PCT Publication Nos. WO 90/15070, WO 92/10092 and WO 93/09668; and Fodor et al. (1991) Science, 251, 767-77), herein incorporated by reference.

In one embodiment, the binding partner is immobilized to the binding surface by the use of a linker (e.g. a homo- or heterobifunctional linker). Linkers suitable for joining biological binding partners are known in the art. For example, a nucleic acid or protein molecule may be linked by any of a variety of linkers including, but not limited to a peptide linker, a straight or branched chain carbon chain linker, or by a heterocyclic carbon linker. Heterobifunctional cross linking reagents such as active esters of N-ethylmaleimide have been widely used (see, for example, Lerner et al. (1981) Proc. Nat. Acad. Sci. USA, 78: 3403-3407 and Kitagawa et al. (1976) J. Biochem., 79: 233-236, and Birch and Lennox (1995) Chapter 4 in Monoclonal Antibodies: Principles and Applications, Wiley-Liss, N.Y.), herein incorporated by reference.

In one example, the binding partner is immobilized utilizing a biotin/avidin interaction. In this embodiment, biotin or avidin with a photolabile protecting group can be exposed to the binding surface on the probe. Irradiation of the surface at a distinct location results in coupling of the biotin or avidin to the surface at that location. Then, a binding partner bearing an avidin or biotin group, respectively, is contacted with the surface, forming a biotin-avidin complex and is thus localized in the irradiated site. To affix multiple different binding partners to different locations, this process can be repeated at each binding partner location.

Another potential photochemical binding approach is described by Sigrist et al. (1992) Bio/Technology, 10: 1026-1028, herein incorporated by reference. In this approach, the interaction of ligands with organic or inorganic surfaces is mediated by photoactivatable polymers with carbene generating trifluoromethyl-aryl-diazirines that serve as linker molecules. Light activation of aryl-diazirino functions at 350 nm yields highly reactive carbenes, and covalent coupling is achieved by simultaneous carbene insertion into both the ligand and the inert surface. Thus, reactive functional groups are not required on either the ligand or supporting material.

Binding partners can be affixed to any location on the surface that contacts the sample during an assay according to the invention. The binding surface on the probe may be varied considerably in form, as may be desired based upon the binding system requirements. For example, the binding surface may be the externally facing surface of the probe. Alternatively or in addition, as previously mentioned the probe may be tubular or may comprise a porous structure to increase the surface area available for the binding partner. A variety of open cell foam structures, among others can significantly increase the effective surface area. Any of a variety of other surface area enhancing design techniques may also be used, such as providing a plurality of axially extending fins, or a plurality of radially outwardly extending circumferential rings in the binding area of the probe.

C. Probe Configurations

1. Catheter-Based Probes

Referring to FIG. 1, there is disclosed a CMC or marker binding and retrieval probe 10 in accordance with one aspect of the present invention. Although the probe 10 will be described primarily in terms of an insert to be temporarily placed down an existing access port or sheath into the cardiovascular system, for retrieving a marker from blood, the present inventors contemplate broader applicability as will be apparent to those of skill in the art in view of the disclosure herein. Existing access ports or sheaths include but are not limited to Hickman catheters, Portacath catheters, peripherally inserted central catheter (PICC) lines, femoral, jugular, or subclavian central venous lines, radial arterial catheters and peripheral venous lines. Furthermore, additional procedures, such as transseptal puncture and transjugular intrahepatic puncture, may be used to access other body sites such as the arterial chambers of the heart or the portal vein, respectively.

For example, the probe may be adapted for direct access to a target site, without the use of a distinct tubular access catheter. In general, whether used with an access sheath or as a stand alone device, the dimensions of the probe can be optimized by persons of skill in the art in view of the present disclosure to suit any of a wide variety of target sites. For example, the probe of the present invention can be used to obtain samples from large and small arteries and veins throughout the cardiovascular system, as well as other lumens, potential spaces, hollow organs and surgically created pathways. Marker (tumor and/or non-tumor) collection may be accomplished in blood vessels, body lumens or cavities, such as the lymphatic system, esophagus, trachea, urethra, ureters, fallopian tubes, intestines, colon, biliary ducts, spinal canal and any other locations accessible by a flexible or rigid probe which may contain a specific binding partner of diagnostic value. The probe 10 may also be adapted for direct advance through solid tissue, such as soft tissue or through bone, for site specific monitoring of a binding partner of interest.

The probe 10 generally comprises an elongate body 16 extending between a proximal end 12 and a distal functional end 14. The length of the body 16 depends upon the desired access site and the desired placement site for the distal end 14. For example, lengths in the area of from about 1 cm to about 20 or 30 cm may be useful in applications that require the catheter to be advanced down a relatively short tubular access sheath. Longer lengths may be used as desired, such as on the order of from about 120 cm to about 140 cm for use in percutaneous access at the femoral artery for placement of the distal end 14 in the vicinity of the coronary artery. Intracranial applications may call for a different catheter shaft length depending upon the vascular access site, as will be apparent to those of skill in the art.

Many markers of interest, however, may be equally retrievable at any point throughout the cardiovascular system, in which case the probe 10 may be adapted to advance down any convenient access port that may have been placed for other diagnostic or therapeutic use. Devices in accordance with the present invention may also be adapted for exposure to blood by coupling to any of a variety of ports on extracorporeal circulation systems as will be apparent to those of skill in the art in view of the disclosure herein.

In the illustrated embodiment, the body 16 is divided into at least a proximal section 33 and a distal binding zone 34. In general, distal binding zone 34 is adapted to carry a binding partner for the marker of interest, as will be discussed below, and may or may not be otherwise structurally distinct from the proximal section 33.

At least the proximal section 33 of body 16 may be produced in accordance with any of a variety of known techniques for manufacturing catheter bodies, depending upon the desired clinical performance. For example, the body 16 may be formed by extrusion of any of a variety of appropriate biocompatible polymeric materials. Known materials for this application include high density polyethylene, polytetrafluoroethylene, nylons, PEEK, PEBAX and a variety of others such as those disclosed in U.S. Pat. No. 5,499,973 to Saab, the disclosure of which is incorporated in its entirety herein by reference. Alternatively, at least a proximal portion or all of the length of body 16 may comprise a spring coil, solid walled hypodermic needle tubing, or braided reinforced wall, as is understood in the catheter and guidewire arts. Whether metal or polymeric or a hybrid, the body 16 may be hollow or solid depending upon the nature of the binding system and other desired capabilities.

In one cardiovascular example, the body 16 is provided with an approximately circular cross-sectional configuration having an external diameter within the range of from about 0.025 inches to about 0.100 inches. In accordance with one embodiment of the invention, the body 16 has an average external diameter of about 0.042 inches (4.2 f) throughout most of its length. Alternatively, generally rectangular, oval or triangular cross-sectional configurations can also be used, as well as other noncircular configurations, depending upon the method of manufacture, desired surface area, flexibility, access pathway and other design considerations that may be relevant for a particular application.

Dimensions outside of the ranges identified above may also be used, provided that the functional consequences of the dimensions are acceptable for the intended purpose of the catheter. For example, the lower limit of the cross section for any portion of body 16 in a given application will be a function of the number of fluid or other functional lumens, if any, contained in the probe, together with the desired surface area to be available for the binding partner, as will be discussed.

Probe body 16 should also have sufficient structural integrity (e.g., column strength or "pushability") to permit the probe to be advanced to a desired target site without buckling or undesirable bending.

The proximal end 12 of the probe 10 may be provided with a grip 46 such as a polymeric cap 48 which may be molded or otherwise secured to the proximal end 12 of the body 16. Preferably, the cap is provided with a complementary surface structure to allow a removable connection between the cap and the proximal end of the IV catheter or other device through which the probe 10 will achieve contact with blood or other body fluid. Removable attachment may be accomplished by using any of a wide variety of clips, twist fasteners such as Luer connectors, interlocking snapfit connectors, or friction fit connectors as will be appreciated by those of skill in the art in view of the disclosure herein.

The axial length of the probe 10 is preferably precisely calibrated to match the particular access catheter with which it is to be used, to provide a reproducible length of the binding zone to be exposed to the sample of interest.

Figure 2:
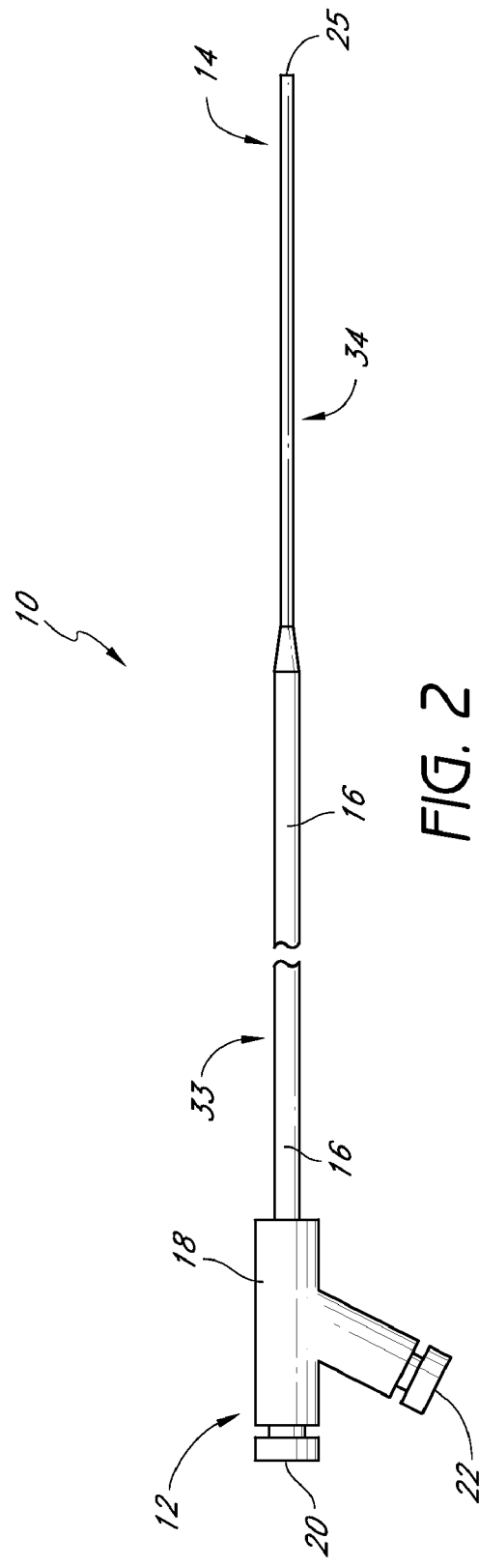
FIG. 2 represents an elevational view of another embodiment of a probe with a guidewire lumen and side port.

Referring to FIG. 2, there is disclosed an alternative implementation of the probe of the present invention. The proximal end 12 of probe 10 is provided with a manifold 18 having one or more access ports as is known in the art. Manifold 18 may be provided with a guidewire port 20 in an embodiment where over-the-wire navigation of the probe may be desired. An infusion port 22 may be provided with or without the guidewire port. The infusion port is in fluid communication with the binding zone through an infusion lumen. This allows periodic or continuous infusion of saline, heparin or other media to prevent "clogging" or coating of the binding zone over time, by natural clotting or other processes which may interfere with the efficacy of the binding chemistry. Additional access ports may be provided as needed, depending upon the desired capabilities of the catheter. Manifold 18 may be injection molded from medical grade plastics or formed in accordance with other techniques known in the art.

The distal end 14 of the probe 10 may be provided with an atraumatic distal tip 25 which may include a guidewire exit port 26 in a guidewire lumen embodiment as is known in the art. A radiopaque marker (not illustrated) may be provided on the probe body 16 in the case of relatively long probes to facilitate positioning of the probe as is known in the art. Suitable marker bands can be produced from a variety of materials, including platinum, gold, and tungsten/rhenium alloy.

The distal zone of the probe is provided with a binding zone, having a binding partner for binding with a marker of interest. As used herein, the term marker refers to any CMC discussed above, as well as any other cell, cell fragment, protein, peptide, glycoprotein, lipid, glycolipid, proteolipid, or other molecular or biological material that is uniquely expressed (e.g. as a cell surface or secreted protein) by diseased cells, or is expressed at a statistically significant, measurably increased or decreased level by diseased cells, or in association with a disease state of interest (e.g. a protein expressed by an infectious agent associated with disease), or is expressed at a statistically significant, measurably increased or decreased level by diseased cells compared to normal cells, or which is expressed by non-diseased cells in association with disease (e.g. in response to the presence of diseased cells or substances produced therefrom). Disease markers can also include specific DNA or RNA sequences marking a deleterious genetic change, conformational change compared to baseline or normal, or an alteration in patterns or levels of gene expression significantly associated with disease. Disease markers include breast cancer markers.

The term cancer marker refers to a subset of disease markers, namely any protein, peptide, glycoprotein (including but not limited to mucins, mucoid and amyloid glycoproteins), lipid, glycolipid, proteolipid, or other molecular or biological material that is uniquely expressed (e.g. as a cell surface or secreted protein) by cancerous cells, or is expressed at a statistically significant, measurably increased or decreased level by cancerous cells compared to normal cells, or which is expressed by non-cancerous cells in association with cancer (e.g. in response to the presence of cancerous cells or substances produced therefrom). Cancer markers can also include specific DNA or RNA sequences marking a deleterious genetic change, conformational change, or an alteration in patterns or levels of gene expression significantly associated with cancer.

a. Binding Zone Surface Area

Figure 3A:
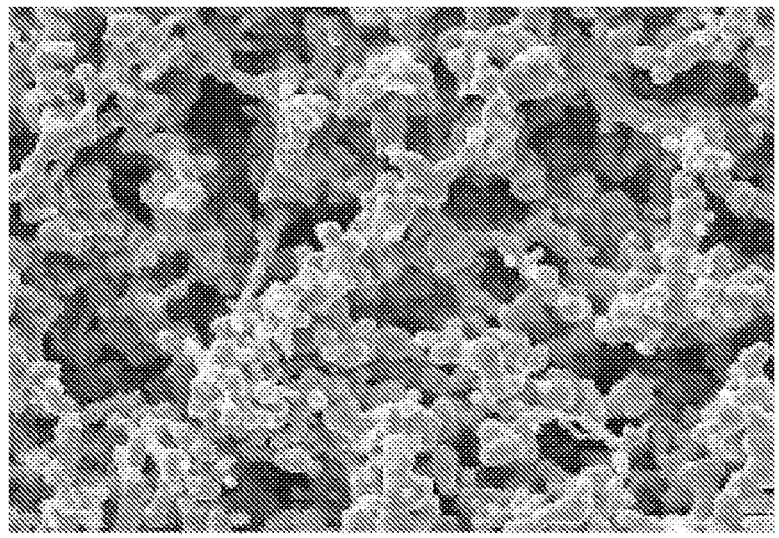
FIGS. 3A and 3B are scanning electron micrographs depicting various embodiments of the invention comprising porous structures.
Figure 3B:
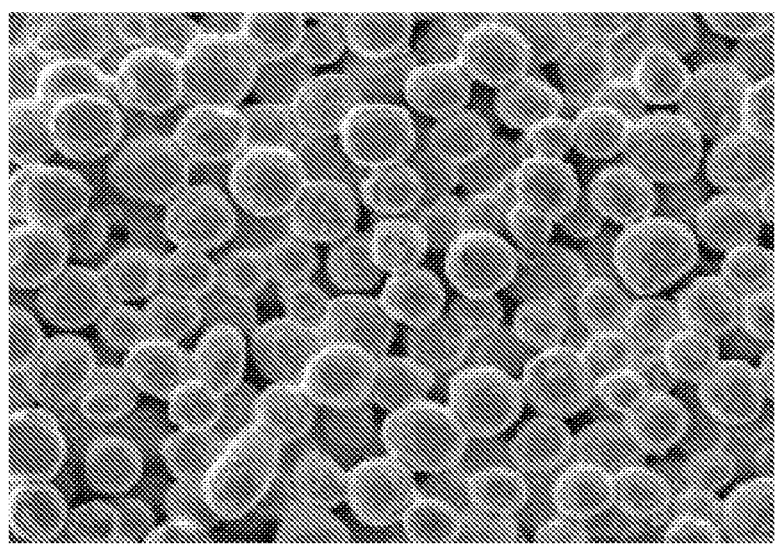
Figure 4A:
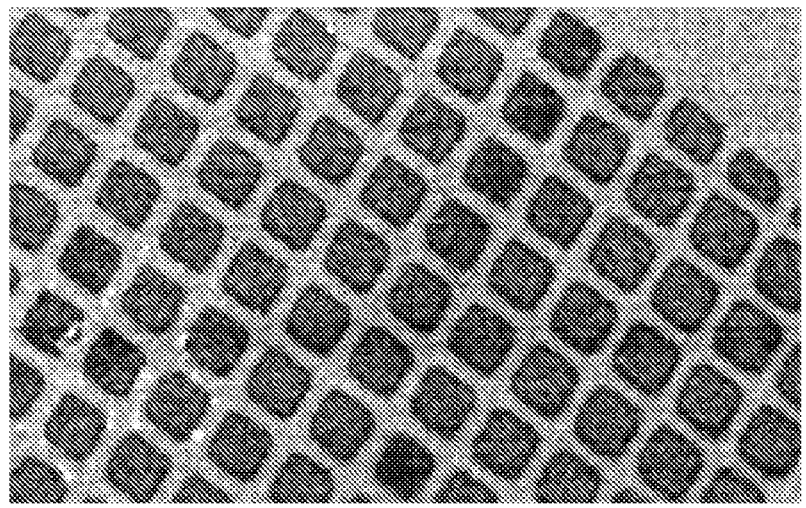
FIGS. 4A through 4D are micrographs illustrating various configurations of the micro-porous tube of a probe.
Figure 4B:
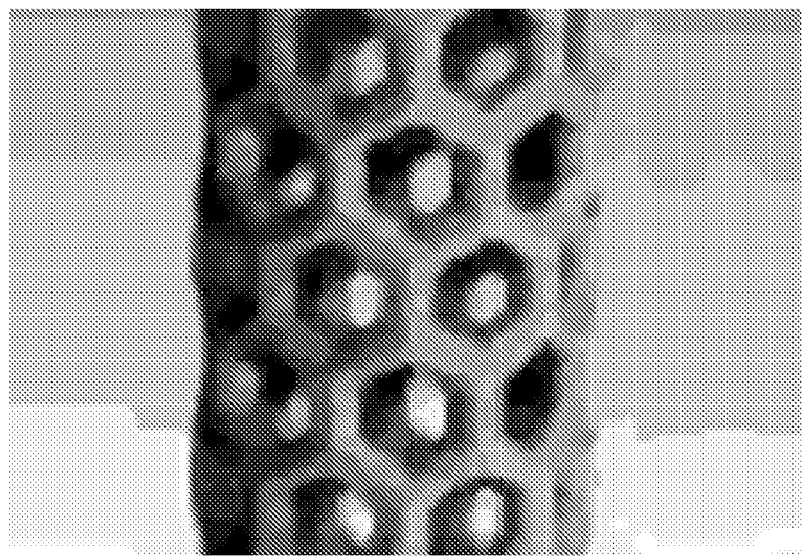
Figure 4C:
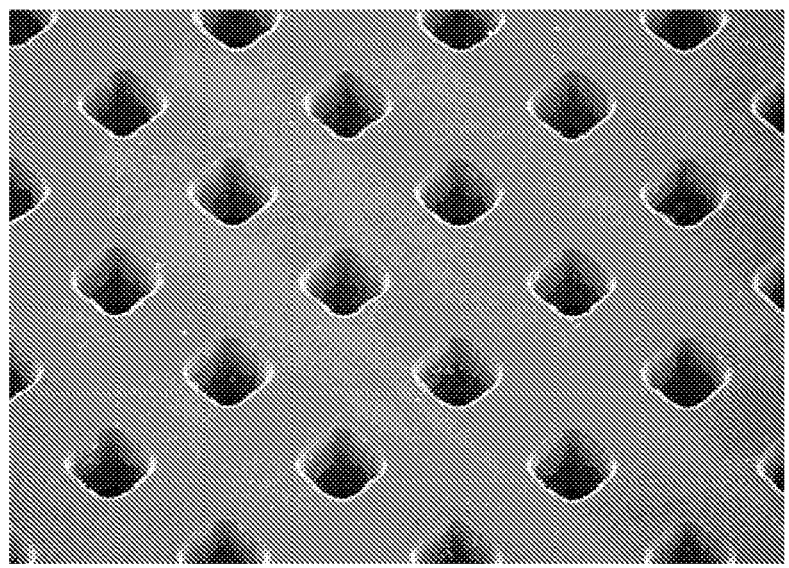
Figure 4D:
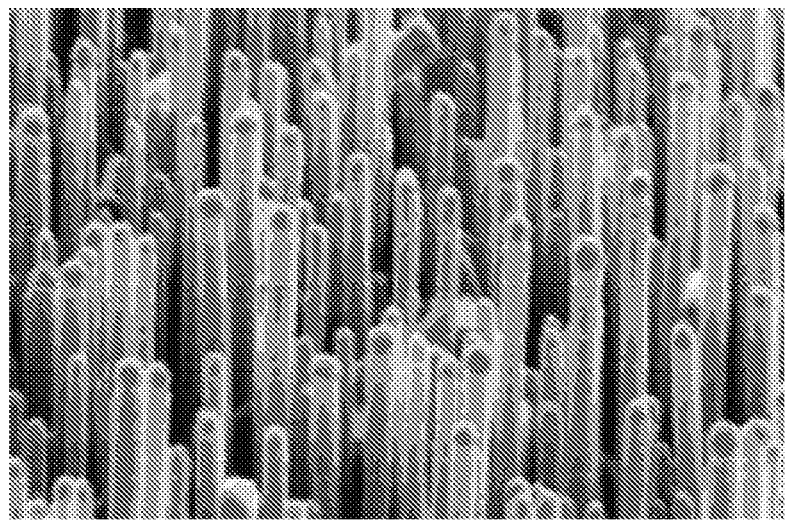

The binding zone may be configured with an increased surface area to provide an increased number of binding sites on the probe. The surface area may be increased by providing an increased longitudinal length, increased diameter or cross-section through at least a portion of the distal zone. In addition, or alternatively, at least a portion of the distal zone may comprise a porous material and/or microstructure to increase the surface area. Non-limiting examples of porous materials include porous polymers, ePTFE, PTFE, polyurethane, silicone, foam, or a ceramic with a porous surface (e.g., titanium nitride, titanium carbide, carbon, and silicon carbide). Various techniques for depositing material on the probe surface to provide a porous structure may also be used and include ion beam deposition, sintering, sputtering, ion implantation, laser surface alloying, electroplating, physical or chemical vapor deposition, chemical or physical etching, grit blasting, plasma and thermal spray coating. Other materials that can be applied to the probe surface include iridium oxide, graphite and platinum black. The surface area may be increased through microstructures on the binding zone surface, formed from processes including but not limited to mechanical roughening of the probe surface, laser drilling or metal sintering onto the probe. The probe may also be manufactured using microporous tubing, porous fabric and polymers, carbon fiber bundles, and nanotubes. The surface area of the binding zone may be configured by one skilled in the art depending upon the expected release pattern, degradation and metabolization pathways and binding kinetics of the CMCs of interest. FIGS. 3A and 3B represent scanning electron micrographs (SEM) of various porous configurations that provide an increased surface area for the probe. FIG. 3A depicts one embodiment of the invention comprising a microporous zone formed by vapor deposition. FIG. 3B depicts another embodiment of the invention formed with sintered metal beads. One skilled in the art will understand that a variety of metals may by used for a sintered porous surface, including but not limited to platinum, platinum/iridium and other platinum group metals or alloys thereof, titanium, titanium alloys and 316L stainless steel. In one embodiment, the sintered metal zone has an average pore size of about 5 microns to about 150 microns to allow particle access into the microporous structure. In other embodiments, an average pore size of about 5 microns to about 100 microns may be used. In one example, a sintered metal porous zone has an average pore size of about 10 microns to about 50 microns. Microporous structures will typically have a porosity between about 10% to about 80%. In some embodiments, the porous layer has a porosity of about 10% to about 60%, and preferably about 40%. Other binding zone structures that increase the surface area are shown in FIGS. 4A through 4D. FIG. 4A is a photograph of a porous fabric. FIG. 4B depicts a porous polymer. FIG. 4C depicts laser drilled holes in a polymer surface and FIG. 4D depicts a nanotube microstructure for providing an increased surface area.

b. Distal Tip Configurations

FIGS. 5A and 5B depict one implementation of the invention, where the body 16 of the probe 10 comprises a proximal section 33 and a distal zone 34 attached through a joint area 50. In one embodiment, the proximal section 33 has an average outer diameter of about 0.5 mm to about 2 mm, but average outer diameters from about 1 mm to about 30 mm may also be used, depending on the desired location and positioning procedure. The proximal section 33 may be made through extrusion or molding using any of a variety of flexible biocompatible polymers including but not limited to PEBAX, polyurethane (Q747), PE, PTFE, nylon, silicone rubber, or combinations thereof. The polymer typically have a hardness within the range of about 80 A to about 75 D, but polymers within other hardness ranges may also be used. In another embodiment, the polymer has a hardness of about 10 D to about 80 D. In one embodiment, the proximal section may have a length of about 20 mm to about 300 mm. In other embodiments, the proximal section may have a length of about 20 cm to about 40 cm, or about 80 cm to about 140 cm, depending on the distance from the insertion point to the target location. The joint area 50 may have any of a variety of configurations for attaching the proximal section 33 and the distal zone 34, including but not limited a male/female configuration or any other mechanical or friction fit known in the art. The proximal section 33 and distal zone 34 may be joined in any of a variety of ways, including but not limited to adhesive bonding with medical grade epoxy, polyurethane adhesives, fast setting glue, UV cure adhesives, solvent fusing or heat fusing. A metallic core may be included in proximal section 33 and/or distal zone 34 to provide sufficient column strength or pushability.

Figure 6B:
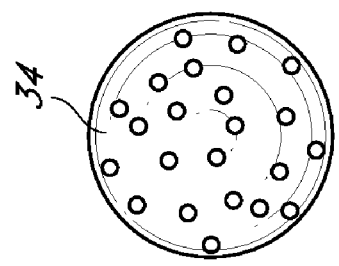
FIGS. 6A and 6B are schematic side and front elevational views of another embodiment of the probe comprising a unitary body design.
Figure 6A:
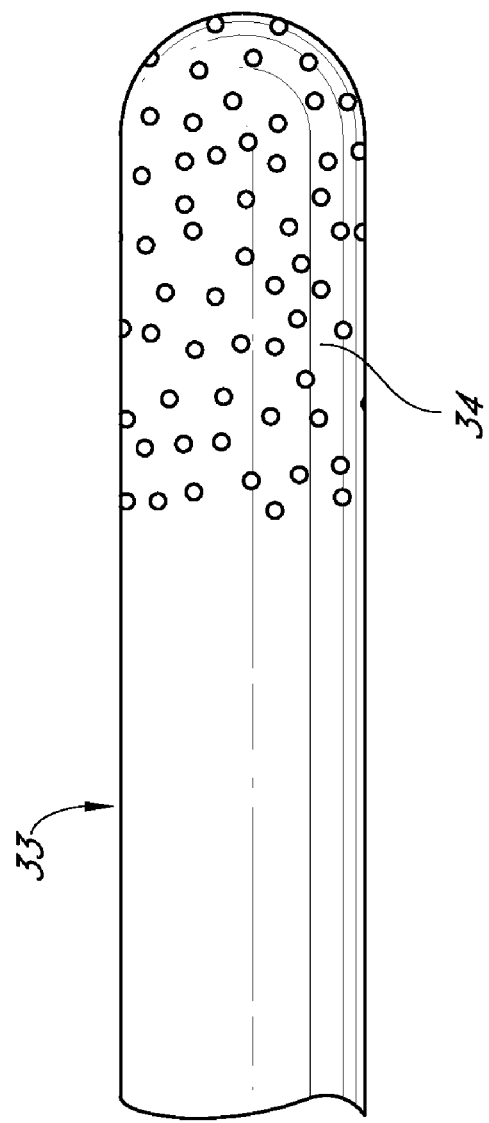

FIGS. 6A and 6B illustrate another embodiment of the invention where the proximal section 33 and the distal zone 34 comprise the same material and therefore, a joint area is not required. If an increased surface area on the distal zone 34 is desired, laser drilling and other methods previously mentioned may be used to alter the surface area.

Figure 7A:
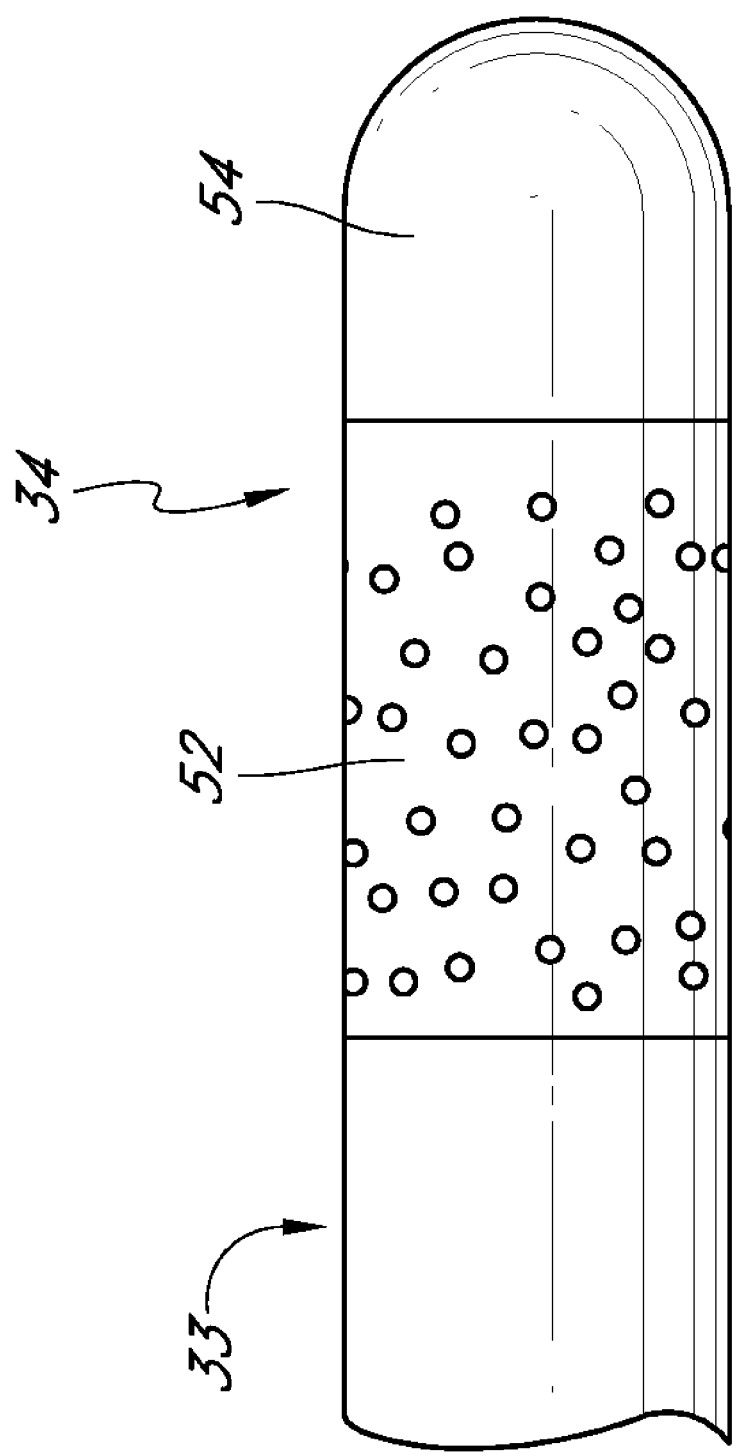
FIGS. 7A and 7B are schematic side and front elevational views of one embodiment of a micro-porous probe with an atraumatic tip.
Figure 7C:
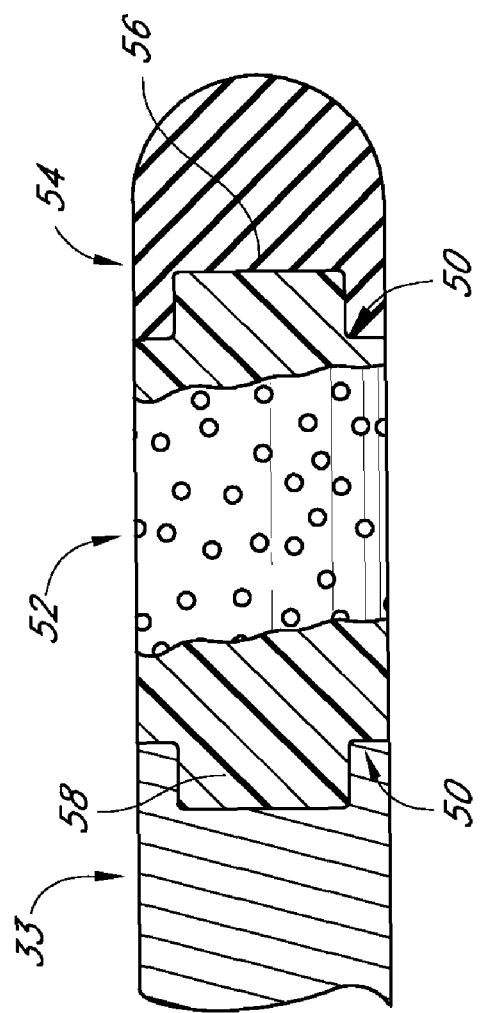
FIG. 7C is a longitudinal cross sectional schematic views of one embodiment of a micro-porous probe in FIG. 7A.
Figure 7B:
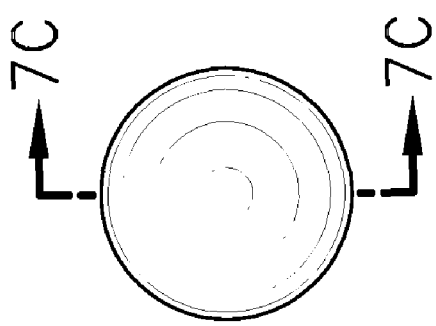

In some embodiments of the invention, an atraumatic tip is provided at the distal end of the probe to reduce potential damage to the probe and the surrounding tissue during insertion. FIGS. 7A through 7C represent one embodiment of the probe comprising an atraumatic tip. Referring to FIG. 7A, the distal zone 34 of the probe 10 comprises a micro-porous segment 52 joined at a joint area 50 to a soft tip 54. The soft tip comprises a distally rounded structure comprising a material such as PEBAX, polyurethane (Q747), silicone rubber, PTFE, nylon, or other biocompatible polymer having a hardness within the range of about 80 A to about 75 D. The soft or atraumatic tip 54 has a length of about 2 mm to about 6 mm and is joined at its proximal end 56 to a porous segment 52 at a joint area 50 using an adhesive such as a polyurethane adhesive, an epoxy, fast setting glue, UV cure adhesive or other adhesives known in the art. The porous segment has a length of about 1 mm to about 10 mm and an average diameter of about 0.5 mm to about 2 mm or more. As illustrated in FIG. 7C, the porous segment 52 may comprise a ring or tubular structure, but other structures with a core may also be used. The porous ring is joined at its proximal end 58 to the proximal section 33 of the probe at another joint area 50 using an adhesive or other joining process.

At least a portion of the porous segment 52 comprises a binding zone for interacting with one or more CMCs. The binding zone of the distal zone may have a diameter of about 0.5 mm to about 2 mm. In another embodiment, the binding zone has an average diameter of about 1 mm to about 5 mm or more. In one embodiment, the binding zone has a length of about 1 mm to about 10 mm. In another embodiment, the binding zone has a length of about 5 mm to about 30 mm or more. The binding zone may comprise a porous material and/or porous microstructure as previously mentioned, such as a sintered metal, a porous ceramic, a sputtered or vacuum deposited metal or ceramic, a porous polymer or a laser-drilled material. Further detail of the binding zone is provided below.

The body 16 of the probe 10 may optionally comprise at least one lumen generally along the length of the body 16 for passing the probe over a guidewire. The lumen may pass from the proximal section 33 to the distal zone 34 and exit the distal end 14 of the probe 10. Alternately, the lumen may terminate prior to the distal end 14 of probe 10 at the exterior surface of the proximal section 33 or distal zone 34, similar to a rapid-exchange catheter.

2. Detachable Probes

In another embodiment of the invention, depicted in FIGS. 8A and 8B, the probe 60 is configured so that it is capable of implantation within the body and does not require a permanent proximal attachment for manipulation and/or retrieval of the probe 60. A detachable or implantable probe 60 may be beneficial where detection of a CMC requires prolonged exposure to the body, but the probe 60 is not limited to this particular use. By detaching from its delivery tool, contact between the probe and the external surface of the body and the probe surface area within the body may be reduced. This may decrease the risk of thrombogenicity and/or infection created by the presence of the probe 60. Those with cancer or a history of cancer or other disease may be predisposed to clot formation and infection and may benefit from additional measures to reduce such risks.

In one embodiment, the probe comprises a binding zone and an engagement interface for reversibly engaging a delivery/retrieval tool. The binding zone comprises at least one site for interacting with one or more CMC. The configuration of the binding zone is described in further detail below. The engagement interface comprises a mechanical or friction interface capable of forming a mechanical or friction fit with a delivery/retrieval tool to facilitate implantation and removal of the probe. The engagement interface may be further configured to orient the probe with respect the delivery/retrieval tool to facilitate positioning and removal of the probe through narrow openings such as a blood vessel. The probe may further comprise a support for maintaining the configuration of the binding zone and resisting deformation of the binding zone. The support may be useful where the binding zone comprises a thin or pliable surface. The probe may optionally comprise an anchor system for maintaining the position of the probe in a general or particular location.

In one embodiment of the invention, the probe 60 comprises a stent support 64 attached to a binding zone jacket 62. The stent-support comprises 64 a first end 66, a second end 68, a lumen 70 between the first end and second end, and may be configured similar to a vascular stent with a mesh-like or zig-zag structure, as shown in FIGS. 8A and 8B. The stent support 64 may be self-expanding or balloon-expandable. One skilled in the art will understand that any of a variety of stent structures, configurations and materials may be used, including but not limited to nitinol, 316L stainless steel, platinum or platinum/iridium. The stent support 64 may be dimensioned for placement in any of a variety of locations, including but not limited to cardiovascular system, a peripheral vein or artery, biliary system, urinary tract, gastrointestinal tract and other lumens or body cavities, natural or artificial. In one embodiment, the stent support has an average diameter of about 0.5 mm to about 2 mm. In another embodiment, the stent support has an average diameter of about 1 mm to about 8 mm. The stent support may have a length of about 5 mm to about 60 mm. In another embodiment, the stent support has a length of about 10 mm to about 30 mm.

A binding zone jacket 62 is attached to at least a portion of the stent support 64. The jacket 62 may surround a portion of the stent support 64 or may be fixed within the lumen 70 of the stent support 64. One or more jackets may be attached to the stent 64. The jacket surface may comprise a biocompatible porous material or porous microstructure to increase the potential binding surface area available. Biocompatible porous materials include but are not limited to PEBAX, polyurethane (Q747), silicone rubber, PTFE and nylon. The configuration of the binding zone jacket is described in further detail below. Alternatively, the binding zone may be directly bonded onto the surface of the stent configuration and a jacket is not required.

Stent retrieval is known in the art and may be performed in several ways. Representative patents include but are not limited to U.S. Pat. No. 6,569,181 to Burns and U.S. Pat. No. 6,187,016 to Hedges et al., herein incorporated in their entirety by reference. The stent support may further comprise one or more engagement elements to facilitate retrieval of the stent from the body by a retrieval tool.

In addition to affixing a binding partner to the binding zone, other molecules or components may be bound to the binding zone to facilitate or support the function of the binding zone. In one embodiment, heparin is bound to the binding zone and possibly other portions of the probe to resist thrombus formation that may increasingly affect the function of the binding partners with extended exposure time to the body. Heparin coating of medical devices is well known in the art, as described by Hsu et al. in U.S. Pat. No. 5,417,969, herein incorporated in its entirety by reference. In another embodiment, a streptokinase coating is provided to resist clot formation (Niku S D et al., Isolation of lymphocytes from clotted blood, J Immunol Methods. 1987 Dec. 4; 105(1):9-14, herein incorporated by reference). Other materials that may be bonded to the binding zone or probe surface include but are not limited to hydrogels or other lubricious coatings, as described by Hostettler et al. in U.S. Pat. No. 5,919,570, and antimicrobial agents, as described by Raad and Sherertz in U.S. Pat. No. 5,688,516, herein incorporated in their entirety by reference. An antimicrobial component may reduce the risk of probe colonization by infectious bacterial and fungal organisms for a probe placed into a body for an extended period of time. Such antimicrobial agents may include but are not limited to aminoglycoside, amphotericin B, ampicillin, carbenicillin, cefazolin, cephalosporin, chloramphenicol, clindamycin, erythromycin, gentamicin, griseofulvin, kanamycin, methicillin, nafcillin, novobiocin, penicillin, polymyxin, rifampin, streptomycin, sulfamethoxazole, sulfonamide, tetracycline, trimethoprim, and vancomycin.

The probe may further comprise an optional elution zone capable of retaining and releasing one or more substances such as drug compounds, reagents or other substances. In one embodiment, the elution zone releases a substance that enhances release of a CMC from the body. In another embodiment, the elution zone releases a substance that facilitates detection of a CMC, including but not limited to Ab labeled fluorescent dyes. In still another embodiment, the elution zone releases a substance capable of reducing a body's immune response to an antigenic element on the probe. In another embodiment, the elution zone is capable of releasing one or more treatment agents for reducing fibrin deposition onto the binding zone and other portions of the probe. Fibrin deposition may decrease or affect the binding of CMCs to their binding partners into the binding zone. Agents that may be released from the elution zone include but are not limited to dexamethasone, paclitaxel, unfractionated heparin, low-molecular weight heparin, enoxaprin, synthetic polysaccharides, ticlopinin, dipyridamole, clopidogrel, fondaparinux, streptokinase, urokinase, r-urokinase, r-prourokinase, rt-PA, APSAC, TNK-rt-PA, reteplase, alteplase, monteplase, lanoplase, pamiteplase, staphylokinase, abciximab, tirofiban, orbofiban, xemilofiban, sibrafiban, roxifiban, bivalirudin, and pentoxifylline.

Alternatively, a chip-based detection system may be used. For example, DNA/oligonucleotide chip detection involves attachment or incorporation of a chip into a device to be inserted into the blood stream or body cavity. The assessment of nucleic acids bound to the chip may be performed in vivo directly through electronic or chemical signaling or ex vivo by a detection device. For DNA analysis this will include microsatellite analysis for loss of heterozygosity (LOH) or by single nucleotide polymorphism (SNP). Other genomic DNA markers can include mutations, amplifications and translocations. The analysis may involve specific or multiple sites of the chromosomal or mitochondrial DNA from tumor cells. RNA analysis will involve assessment of mRNA of transcripts of specific genes related to the tumor cells. The mRNA transcript may be of the whole or part of the full transcript or a truncated derivative of the transcript. The procedure may also include chromatin and DNA complexes (histone proteins) related to specific genomic regions of tumor cells. The procedure may encompass assessing acetylation and deacetylation of chromatin regions of specific genomic regions, methylated or non-methylated. The procedure may encompass assessing methylated or non-methylated regions of the genomic regions such as promoter related-regions of tumor-related genes. The chip may be inserted for 30 min, 1, 2, 3 . . . 24 hr and removed for assessment or assessed directly.

D. Insertion and Placement of Collection Probe

The collection probe may be inserted in a variety of ways and to variety of locations within the body. In some situations, the probe may be inserted during a cancer surgery where access to sentinel sites of disease recurrence is readily accessible. For instance, following a mastectomy and axillary node dissection for breast cancer, a collecting probe may be implanted during the same procedure into the lymphatic ducts draining the breast. Such as site may provide earlier detection of recurring disease and may also increase the yield from such surveillance. Similarly, placement of the collection probe surgically may also allow or subcutaneous implantation into a large vein while the patient is still under anesthesia, thereby decreasing the risk of infecting the device compared to percutaneous insertion.

The device may also be configured for percutaneous insertion. Some embodiments of the device allow insertion of the probe into existing long-term access sites such as a Hickman catheter, Portacath, or a peripherally inserted central catheter (PICC) line or variants thereof. Similarly, the probe may also be configured for insertion through central venous catheters inserted into the femoral or jugular vein, or large-bore IV access site. For example, a Portacath is an implantable venous access device that is frequently used in cancer patients to provide long-term vascular access for chemotherapy. A detection probe placed into a Portacath or a Portacath variant may serve a dual function of treating the cancer and provide the ability to monitor treatment effect.

In use, a probe having at least one binding partner is provided. The probe is advanced to a site where a binding zone on the probe will be exposed to a carrier such as blood which may periodically contain a marker of interest. The probe is left in place for an evaluation period, to allow the marker to become bound to the binding partner. The probe is thereafter withdrawn, and evaluated to determine the presence of any marker carried by the binding zone.

In one application, the probe is advanced through an access tube to position the binding zone at an intralumenal site within an artery or vein. The binding zone is left at the site for an evaluation period of generally at least about one hour, in come applications at least about four or six hours, and for certain markers at least about 12 hours or 24 hours or more. This allows collection of at least a first quantity of a target marker from a first release of marker into the blood, and in certain applications at least also a second quantity of the target marker from a second release of marker into the blood, the first and second releases separated in time from each other. The first and second quantities of the target marker may be collected on the same probe. Alternatively, during the evaluation period, a first probe may be withdrawn from the site and replaced by at least a second probe, which carries the same or a second binding partner.

The device may be inserted through any of a variety of access methods known to interventional radiology, cardiology, gastroenterology and other medical and veterinary disciplines. These procedures may include but are not limited to endoscopic retrograde cholangiopancreatography (ERCP) for placement into the biliary tree or pancreas, transseptal puncture for placement into the arterial portion of the cardiovascular system, lumbar puncture into the cerebrospinal fluid, and cystoscopy for placement into the urinary tract.

E. Ex Vivo Probe Assessment

The capture of nucleic acids from an in vivo device can be monitored ex vivo using standard qualitative and quantitative molecular assays. The assays can directly measure the nucleic acids or amplify them to measure them. The assays can be probe-, sequence- or affinity ligand-based. The assessment of DNA/RNA in body fluids ex vivo is known and currently available. These include but are not limited to gel electrophoresis, real time quantitative polymerase chain reaction (PCR), probe based chromatographic assays. For DNA analysis, this will include microsatellite analysis for loss of heterozygosity or by single nucleotide polymorphism (SNP). Other DNA markers can include mutations, amplifications, insertions and translocations. This may be specific or multiple sites of the DNA from tumor cells. RNA analysis will involve assessment of mRNA of transcripts of specific genes related to the tumor cells. The mRNA transcript may be of the whole or part of the full transcript or a truncated derivative of the transcript. The procedure may also include chromatin and DNA complexes related to specific genomic regions of tumor cells. The procedure may also include assessment of acetylated and de-acetylated or modified regions of the chromatin and histones surrounding a specific gene. The procedure may also include assessment of methylation or demethylation of gene promoter regions.

Assessment of antibody or protein-based markers is currently available and may include but is not limited to affinity binding assays, mass spectroscopy, and ELISA. Similarly, of carbohydrate markers is also known and may include affinity or ligand-based capture assays and mass spectroscopy. One skilled in the art can select one or more assays based upon the particular marker or markers of interest.

One embodiment of the invention comprises a percutaneously insertable device affixed with antibodies that recognize tumor-related cell surface proteins/glycoproteins (i.e.: cMet, HER2/neu, beta-Human chorionic gonadotropin (HCG), MUC-1, etc) or glycolipids (gangliosides GM2, GD2). The antibodies can capture and bind the circulating tumor cells in the blood or body fluid. Single or multiple antibodies to a specific cell surface marker or multiple markers may be used. The capture device or catheter with the bound tumor cells can be removed and subjected to standard ex vivo isolation methods known in the art for RNA, DNA, carbohydrate and protein isolation and purification. The isolation of these cell products is one approach to identify their specificity. Another approach is to isolate the cells and assess them as whole cells. These approaches are advantageous in providing a unique in vivo enrichment method for the collection of circulating tumor cells and their subcomponents, such as DNA, RNA and proteins, for further evaluation and assessment.

In some embodiments, the cells can be removed physically, biochemically or eluted off the device by competitive reagents to the antibody. Preferably, once eluted, the cells can undergo respective component isolation. In other embodiments, the cells are analyzed while still attached to the device. In one example, cells can be processed, purified and quantitated for specific nucleic acids such as RNA and DNA by methods known in the art. To assess the amount of nucleic acids, one can perform qualitative and/or quantitative analysis for specific RNA and DNA markers that are tumor-related. These markers may be different from the antibody specific markers that are used to capture the cells. The antibody used to capture markers may also be used.

In one embodiment, cell capture with antibody to c-Met is performed and then assessment for cMet mRNA expression is performed qualitatively or quantitatively by realtime PCR. PCR provides amplification of the target mRNA marker and allows for detection through many available approaches including but not limited to as gel electrophoresis, realtime PCR thermocyclers, etc.

In one embodiment, tumor mRNA markers for assessment can include markers most prevalent in the type of cancer being assessed, but less prevalent markers may also be used. For example, in melanoma one could assess for MART-1 mRNA. For breast cancer one can assess mammoglobin. Quantitative marker detection may be used to rule out false positives. This provides another layer of specificity to the detection scheme. Also, to increase the sensitivity of the detection scheme, multiple markers can be used to assess for isolated tumor cells. One can also assess for specific DNA markers such as mutations, loss of heterozygosity, amplification, translocation, etc. Specific genetic changes may be related to specific cancers or groups of cancers. Specific genetic changes can be used in combination with multiple marker detection approaches. Some examples include detection of BRAF mutation at V600 for melanoma, methylation of RASSF1a promoter site, or LOH at 9p21. The use of specific nucleic markers can be used to determine specific types of cancers, level of disease malignancy, disease aggressiveness, prognostic and predictive values and other information.

In one approach, proteins are isolated and purified by direct isolation. These proteins can be assessed by ELISA for specific tumor markers, Western Blot approaches, mass spectrometry, protein arrays, ProteinChips, antibody based assays, affinity protein based assays, etc in a quantitative and qualitative manner. The approaches can be used for glycoproteins and other carbohydrate markers. The use of specific protein/glycoprotein/carbohydrate markers can be used to determine specific types of cancers, level of disease malignancy, disease aggressiveness, prognostic and predictive values and other information.

Another approach is to elute the cells. Cells bound to the catheter can be evaluated using conventional histopathologic and immunocytochemical staining methods that characterize the collected cells of interest. These cells can be evaluated directly on the catheter or, in one embodiment, the cells are isolated from the catheter using standard methods to disrupt tumor cell complementary antibody binding through current methods of mechanical separation (such as scraping and/or washings with saline, buffered solutions, or media). In another embodiment, chemical dissociation techniques are used and include washing the catheter/antibody/tumor cell complex with pH buffered solutions (such as PBS with EDTA or salts that disrupt antibody binding to cells but not destroy the cells, etc.), thus allowing the cells to be collected intact after separation from the catheter/antibody complex and assessed by conventional methods such as immunostaining procedures. In still another embodiment, cells may also be released by disrupting the antibody-cell complex from the device. After isolation, the cells can be immunostained with specific antibodies against tumor cell surface markers or intracellular markers. The assessment of tumor cells may be performed by conventional immunopathology for tumor cell diagnosis, but other approaches are known in the art, including but no limited to immunostained cells by FACs analysis. In these approaches, multiple antibodies can be used for detection to improve sensitivity and specificity for specific cells. Also, some approaches allow detection of the number of cells detected for quantitation of disease level. Cells can be also assessed by conventional or non-conventional stains and dyes that are not antibody-based. Still another approach is in situ hybridization with nucleic acids or derivative molecules that are complimentary. The above approaches for detection of eluted cells, intact or not intact, for specific components (protein, nucleic acids, etc) can be approached quantitatively or qualitatively. The approaches can be by individual or combination of methods.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method for collecting biological markers, comprising the steps of:
providing a collecting probe comprising a binding surface, wherein the binding surface comprises an outer porous zone and an inner non-porous zone, wherein the porous zone has affixed thereto at least one binding agent for binding a marker, and wherein the porous zone is configured to immobilize a marker to the binding surface upon binding of the marker to the binding agent, thereby increasing the surface area of the binding surface;
positioning at least a portion of the probe in an anatomical structure of a living organism;
maintaining the probe in a generally fixed position for greater than 1 hour; and
removing the probe from the living organism.

2. The method of claim 1, further comprising:
binding at least one marker at a first point in time; and
binding at least one marker at a second point in time, wherein the collecting probe remains in the generally fixed position between the first and second point in time, wherein upon binding the at least one marker at a first point in time, the marker is immobilized and bound to the binding surface.

3. The method of claim 1, further comprising:
binding at least one marker at about a first peak in marker concentration; and
binding at least one marker at about a second peak in marker concentration, wherein the collecting probe remains in the generally fixed position between the first and second peak in marker concentration.

4. The method of claim 1, further comprising analyzing the probe for markers bound to the binding agent.

5. The method of claim 4, wherein the analyzing step is performed ex vivo.

6. The method of claim 1, wherein the porous zone comprises a microporous surface.

7. The method of claim 6, wherein the microporous surface comprises a material selected from the group consisting of a microporous polymer, a nanotube, metal, non-metal, ceramic, and a combination thereof.

8. The method of claim 7, wherein the microporous surface is formed by at least one process selected from the group consisting of vapor deposition, physical vapor deposition, chemical vapor deposition, sputtering, reactive sputtering, sintering, vacuum deposition, ion beam deposition, ion implantation, laser surface alloying, electroplating, chemical etching, physical etching, grit blasting, plasma spray coating, thermal spray coating, mechanical roughening, laser drilling, and metal sintering.

9. The method of claim 8, wherein the microporous surface is formed by laser drilling.

10. The method of claim 1, further comprising implanting at least a portion of the collecting probe in the anatomical structure of the living organism.

11. The method of claim 1, wherein the binding surface is in continuous contact with a circulating body fluid within the living organism.

12. The method of claim 1, wherein the collecting probe further comprises at least one agent selected from the group consisting of: an anti-thrombotic agent, and an antimicrobial agent.

13. The method of claim 1, wherein the marker is a low-level marker in the blood.

14. The method of claim 1, wherein the collecting probe comprises at least one structure selected from the group consisting of: a capture vessel, a tube, a capture filter, and an entrapment device.

15. The method of claim 1, comprising maintaining the probe in the generally fixed position for more than about 2 hours.

16. The method of claim 1, comprising maintaining the probe in the generally fixed position for more than about 4 hours.

17. The method of claim 1, comprising maintaining the probe in the generally fixed position for more than about 24 hours.

18. The method of claim 1, comprising maintaining the probe in the generally fixed position for more than about one week.

19. A method for collecting biological markers, comprising the steps of:
providing a collecting probe comprising a microconfigured binding surface and at least one binding agent affixed to the binding surface for binding a marker, wherein the microconfigured binding surface is directly bonded onto a solid surface of the probe, and wherein the microconfigured binding surface is configured to immobilize the marker to the binding surface upon binding of the marker to the binding agent;
delivering the probe to an anatomical structure of a living organism using a delivery tool, thereby placing the microconfigured binding surface into direct contact with a circulating body fluid in the living organism;
detaching the probe from the delivery tool;
removing the delivery tool from the anatomical structure of the living organism;
maintaining the probe in a general position for a specified period of time; and
removing the probe from the living organism.

20. The method of claim 19, wherein the microconfigured binding surface is a microporous surface.

21. The method of claim 20, wherein the microporous surface comprises a material selected from the group consisting of a microporous polymer, a nanotube, metal, non-metal, ceramic, and a combination thereof.

22. The method of claim 21, wherein the microporous surface is formed by at least one process selected from the group consisting of vapor deposition, physical vapor deposition, chemical vapor deposition, sputtering, reactive sputtering, sintering, vacuum deposition, ion beam deposition, ion implantation, laser surface alloying, electroplating, chemical etching, physical etching, grit blasting, plasma spray coating, thermal spray coating, mechanical roughening, laser drilling, and metal sintering.

23. The method of claim 22, wherein the microporous surface is formed by laser drilling.

* * * * *